(12) United States Patent
Oku et al.

(10) Patent No.: US 8,367,365 B2
(45) Date of Patent: Feb. 5, 2013

(54) METHOD FOR DETERMINING CARBOHYDRATE AND KIT FOR DETERMINING CARBOHYDRATE

(75) Inventors: Tuneyuki Oku, Nishisonogi-gun (JP); Sadako Nakamura, Nishisonogi-gun (JP)

(73) Assignee: Nagasaki Prefectural and Municipal Univ. Corp., Nagasaki (JP)

( * ) Notice: Subject to any disclaimer, the term of this patent is extended or adjusted under 35 U.S.C. 154(b) by 0 days.

(21) Appl. No.: 12/991,606

(22) PCT Filed: May 6, 2008

(86) PCT No.: PCT/JP2008/058440
§ 371 (c)(1),
(2), (4) Date: Nov. 8, 2010

(87) PCT Pub. No.: WO2009/136432
PCT Pub. Date: Nov. 12, 2009

(65) Prior Publication Data
US 2011/0059474 A1    Mar. 10, 2011

(51) Int. Cl.
*C12Q 1/40* (2006.01)
*C12Q 1/37* (2006.01)
*C12Q 1/34* (2006.01)

(52) U.S. Cl. ................ 435/22; 435/23; 435/18
(58) Field of Classification Search .............. 435/22, 435/23, 18
See application file for complete search history.

(56) References Cited

U.S. PATENT DOCUMENTS

| | | | |
|---|---|---|---|
| 4,259,358 A * | 3/1981 | Duthie | 426/46 |
| 5,681,826 A | 10/1997 | Shibuya et al. | |
| 5,789,392 A | 8/1998 | Shibuya et al. | |
| 7,732,426 B2 | 6/2010 | Watanabe et al. | |
| 2008/0131468 A1 | 6/2008 | Watanabe et al. | |

FOREIGN PATENT DOCUMENTS

| | | |
|---|---|---|
| EP | 0690130 A1 | 1/1996 |
| JP | 10-150934 A | 6/1998 |
| JP | 3183500 B2 | 7/2001 |
| WO | 2006/035725 A1 | 4/2006 |

OTHER PUBLICATIONS

Sambucetti M.E. and Zuleta A. Resistant Starch in Dietary Fiber Values Measured by the AOAC Method in Different Cereals. Cereal Chem. (1996) 73:759-761.*
Lee M, Russel R.M., Montgomery R.K., Krasinski S.D. Total Intestinal Lactase and Sucrase Activities are Reduced in Aged Rats. J of Nutrition (1997) 127: 1382-1387.*
Jones et al (Glucose absorption from starch hydrolysates in the human jejunum. Gut.1983. 24: 1152-1160).*
Gray et al. Starch Digestion and Adsorption in Nonruminants. American Institute of Nutrition. 1993. 172-177).*
Jones et al. Glucose absorption from starch hydrosylates in the human jejunum. Gut, 1983. 24: 1152-1160.*
Wilson et al. Adaptation of the duodenum and ileum of the rat to mid-gut resection: enzyme activity and trace metal status. The American Journal of Clinical Nutrition., 1986 43: 185-193.*
Dahlqvist et al. (Separation and Characterization of Two Rat-Intestinal Amylases. Biochem. 1963 89: 272-277).*
McCleary, Barry V. "An integrated procedure for the measurement of total dietary fibre (including resistant starch), non-digestible oligosaccharides and available carbohydrates," Analytical and Bioanalytical Chemistry, Sep. 2007, vol. 389, No. 1, pp. 291-308.
Chonan, Osamu et al "Undigestibility of Galactooligosaccharides," Nippon Shokuhin Kagaku Kogaku Kaishi, Accepted Oct. 2, 2003, vol. 51, No. 1, pp. 28-33.
International Search Report of PCT/JP2008/058440, date of mailing Jun. 3, 2008.

* cited by examiner

*Primary Examiner* — Karen Cochrane Carlson
*Assistant Examiner* — Natalie Moss
(74) *Attorney, Agent, or Firm* — Westerman, Hattori, Daniels & Adrian, LLP

(57) ABSTRACT

It is intended to provide a method for determining a carbohydrate which enables more accurate determination of a carbohydrate. The invention for achieving this object is directed to a method for determining a carbohydrate using a digestive enzyme, characterized in that as the digestive enzyme, an animal-derived low-molecular-weight carbohydrate digestive enzyme is used. More specifically, the invention is directed to a method for determining a carbohydrate using a digestive enzyme, characterized by comprising a first reaction step using thermostable α-amylase; a second reaction step using protease and amyloglucosidase; and a third reaction step using an animal-derived low-molecular-weight carbohydrate digestive enzyme.

6 Claims, 6 Drawing Sheets

METHOD FOR DETERMINING CARBOHYDRATE AND KIT FOR DETERMINING CARBOHYDRATE

TECHNICAL FIELD

The present invention relates to a method for determining a carbohydrate using a low-molecular-weight carbohydrate digestive enzyme and a kit for determining a carbohydrate including a low-molecular-weight carbohydrate digestive enzyme. More specifically, the present invention relates to a method for determining an oligosaccharide (digestible oligosaccharide, nondigestible oligosaccharide) using an animal-derived low-molecular-weight carbohydrate digestive enzyme and a kit for determining an oligosaccharide (digestible oligosaccharide, nondigestible oligosaccharide) including an animal-derived low-molecular-weight carbohydrate digestive enzyme.

BACKGROUND ART

In recent years, there has been a growing interest in being health conscious among people and thus oligosaccharides, which are sweet carbohydrates having physiological effects different from those of sugars, have been actively developed. Oligosaccharides generally have two or more and less than ten constituent sugars in a polymerized form. There are oligosaccharides that are digested by a digestive enzyme (digestible oligosaccharides) and oligosaccharides that are not digested or are not easily digested to a high degree (nondigestible oligosaccharides). Most oligosaccharides with added values to health that have been developed are not digested by a digestive enzyme or are nondigestible oligosaccharides that are not easily digested to a high degree.

Nondigestible oligosaccharides are used in health foods such as foods for specified health uses. These nondigestible oligosaccharides are metabolized through a pathway different from that of digestible carbohydrates such as sucrose and starch. A nondigestible oligosaccharide taken orally reaches the large intestine without being digested by α-amylase or a small intestinal mucosal disaccharidases. In the large intestine, the nondigestible oligosaccharide is fermented by indigenous intestinal bacteria and metabolized into short-chain fatty acids such as acetate, propionate, and n-butyrate, carbon dioxide, hydrogen gas, methane gas, bacterial cell components, and the like. Among them, short-chain fatty acids are absorbed from the large intestine and used solely as the energy source of the host. That is, even carbohydrates that are not digested and absorbed provide energy to a living body by being fermented and absorbed in the large intestine.

At present, 741 items have been approved as foods for specified health uses, and 93 items contain nondigestible oligosaccharides (as of Nov. 26, 2007). Nine kinds of nondigestible oligosaccharides are used in the foods for specified health uses as components involved. However, the determination thereof is performed by original methods of manufacturers, and a standard determination method has yet to be established. The reason for this is as follows. Nondigestible oligosaccharides contain not only oligosaccharides that are not easily digested in the small intestine to a high degree but also oligosaccharides that are partly digested. Therefore, since nondigestible oligosaccharides have constituent sugars and structures different from each other, there are differences in the stability of each of the oligosaccharides and the action mechanism of hydrolases.

An enzyme-gravimetric method of Prosky, which is a dietary fiber determination method, is a method in which digestible carbohydrates and proteins are completely digested by hydrolases and the weight of the undigested matter left and having a large molecular weight is measured. Dietary fiber, which is a high polymer, can be determined by an established method such as the enzyme-gravimetric method of Prosky, but nondigestible oligosaccharides and sugar alcohols, which are low-molecular-weight compounds, cannot be determined by the enzyme-gravimetric method. In recent years, nondigestible oligosaccharides and sugar alcohols have been used in various health foods. Thus, a determination method that can also determine such nondigestible oligosaccharides and sugar alcohols has been considered.

One of the methods for determining a nondigestible oligosaccharide that are approved in AOAC (Association of Official Analytical Chemists) is an enzymatic-HPLC method achieved by partly changing the dietary fiber determination method that uses the enzyme-gravimetric method of Prosky (refer to FIG. 6). As shown in FIG. 6, the enzymatic-HPLC method is a method in which, as in the dietary fiber determination method, digestible components are hydrolyzed by hydrolases and then nondigestible low-molecular-weight substances that are not precipitated with 78% of ethanol are analyzed and determined by HPLC using a specific column. In this method, because an enzyme treatment process in a gastrointestinal tract of a living body is assumed, the amount of nondigestible oligosaccharides that reach the large intestine without being digested in the small intestine, that is, the amount of nondigestible oligosaccharides that are utilized by intestinal bacteria can be estimated.

[Patent Document 1] Japanese Patent No. 3183500

DISCLOSURE OF INVENTION

Problems to be Solved by the Invention

However, it is believed that thermostable α-amylase and amyloglucosidase, which are carbohydrate digestive enzymes used in the enzymatic-HPLC method, can digest high-molecular-weight polysaccharides, but cannot easily digest low-molecular-weight carbohydrates such as an oligosaccharide due to the nature of such enzymes. In fact, when humans take in fructooligosaccharide and isomaltooligosaccharide, which are believed to be nondigestible oligosaccharides, breath hydrogen gas produced through only the fermentation caused by intestinal bacteria excrete about two hours after the intake of the fructooligosaccharide and the amount of hydrogen gas reaches its peak in three to four hours. On the other hand, breath hydrogen gas is hardly observed for the isomaltooligosaccharide. Furthermore, the no-observable-effect level of the fructooligosaccharide on transient diarrhea is 0.3 to 0.4 g/kg body weight whereas the no-observable-effect level of the isomaltooligosaccharide is 1.2 g/kg body weight or more, which is significantly higher than that of an oligosaccharide that is not digested. These reports suggest that fructooligosaccharide is not digested, but isomaltooligosaccharide is digested.

When isomaltooligosaccharide is determined by the enzymatic-HPLC method that is an AOAC official method, isomaltooligosaccharide that is normally believed to be digested is detected as an nondigestible oligosaccharide because "low-molecular-weight carbohydrates such as an oligosaccharide are not easily digested due to the nature of such enzymes" as described above. This clearly suggests that the enzymatic-HPLC method has a problem. The digestive enzymes used in the enzymatic-HPLC method do not include β-galactosidase, whereby lactose or the like that should be digested may be determined as a nondigestible oligosaccharide.

In other words, the enzymatic-HPLC method that is an AOAC official method has a problem in that both nondigestible oligosaccharides and digestible oligosaccharides are determined as nondigestible oligosaccharides.

Accordingly, in order to solve the above-described problem of the related art, an object of the present invention is to provide a method for determining a carbohydrate which enables more accurate determination of a carbohydrate. Another object of the present invention is to provide a kit for determining a carbohydrate which enables more accurate determination of a carbohydrate.

Means for Solving the Problems

In order to solve the above-described problem, the present invention provides a method for determining a carbohydrate using a digestive enzyme, characterized in that the digestive enzyme is an animal-derived low-molecular-weight carbohydrate digestive enzyme.

In order to solve the above-described problem, the present invention also provides a method for determining a carbohydrate using a digestive enzyme, characterized by including a first reaction step using thermostable α-amylase, a second reaction step using protease and amyloglucosidase, and a third reaction step using an animal-derived low-molecular-weight carbohydrate digestive enzyme.

In the method for determining a carbohydrate according to the present invention, an animal-derived small intestinal mucosal hydrolase is preferably used as the low-molecular-weight carbohydrate digestive enzyme.

In order to solve the above-described problem, the present invention also provides a kit for determining a carbohydrate including a digestive enzyme, characterized by including an animal-derived low-molecular-weight carbohydrate digestive enzyme as the digestive enzyme.

In the kit for determining a carbohydrate according to the present invention, an animal-derived small intestinal mucosal hydrolase is preferably included as the digestive enzyme. More specifically, the kit for determining a carbohydrate according to the present invention preferably includes thermostable α-amylase, protease, amyloglucosidase, and an animal-derived small intestinal mucosal hydrolase as the digestive enzyme.

Advantages

According to the present invention, a method for determining a carbohydrate which enables more accurate determination of a carbohydrate can be obtained. Furthermore, according to the present invention, a kit for determining a carbohydrate which enables more accurate determination of a carbohydrate can be obtained.

BEST MODES FOR CARRYING OUT THE INVENTION

Figure 1:
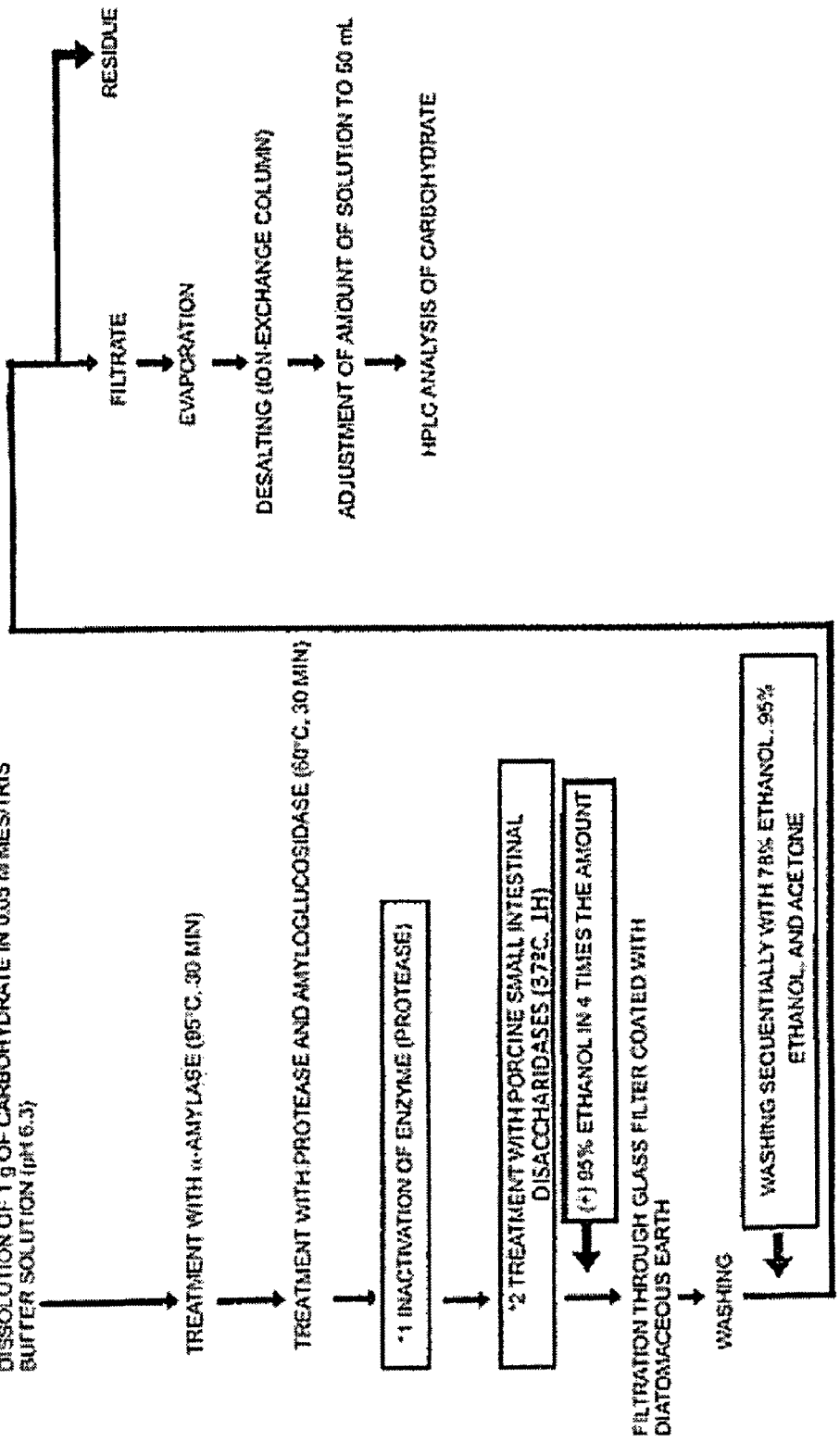
FIG. 1 shows a procedure of a method for determining a carbohydrate according to Example 1 of the present invention. Digestion performed by small intestinal disaccharidase purified from porcine small intestinal mucosal brush border was newly added. "*1" indicates that protease was inactivated such that porcine small intestinal mucosal disaccharidase was not decomposed by protease. "*2" indicates that after that, porcine small intestinal mucosal disaccharidase was caused to react.

Hereinafter, embodiments of the present invention will be described.

A method for determining a carbohydrate according to a first embodiment of the present invention is a method for determining a carbohydrate using a digestive enzyme, characterized in that an animal-derived low-molecular-weight carbohydrate digestive enzyme is used as the digestive enzyme.

A method for determining a carbohydrate according to a second embodiment of the present invention is a method for determining a carbohydrate using a digestive enzyme, characterized by including a first reaction step using thermostable α-amylase, a second reaction step using protease and amyloglucosidase, and a third reaction step using an animal-derived low-molecular-weight carbohydrate digestive enzyme.

In a third embodiment of the present invention, there is provided the method for determining a carbohydrate according to the first or second embodiment, characterized in that an animal-derived small intestinal mucosal hydrolase is used as the low-molecular-weight carbohydrate digestive enzyme.

A kit for determining a carbohydrate according to a fourth embodiment of the present invention is a kit for determining a carbohydrate including a digestive enzyme, characterized by including an animal-derived low-molecular-weight carbohydrate digestive enzyme as the digestive enzyme.

In a fifth embodiment of the present invention, there is provided the kit for determining a carbohydrate according to the fourth embodiment, characterized in that an animal-derived small intestinal mucosal hydrolase is included as the digestive enzyme.

That is, the method for determining a carbohydrate according to this embodiment described above is a method for determining a carbohydrate using a digestive enzyme, characterized in that an animal-derived low-molecular-weight carbohydrate digestive enzyme is used as the digestive enzyme. More specifically, an animal-derived low-molecular-weight carbohydrate digestive enzyme is added to an enzyme reaction system in the method for determining a carbohydrate according to this embodiment. The kit for determining a carbohydrate according to this embodiment may have any configuration as long as the above-described method for determining a carbohydrate can be performed using the kit, and includes an animal-derived low-molecular-weight carbohydrate digestive enzyme as the digestive enzyme. In the present invention (e.g., each of the embodiments described above and Examples described below), an "animal" is a concept that excludes a microorganism. In other words, an "animal-derived low-molecular-weight carbohydrate digestive enzyme" is a concept that excludes a "microorganism-derived low-molecular-weight carbohydrate digestive enzyme".

In the method for determining a carbohydrate according to the embodiment of the present invention and the method for determining a carbohydrate according to Examples described below, a suspension of porcine small intestinal mucosal brush border membrane is used as the animal-derived low-molecular-weight carbohydrate digestive enzyme. Hereinafter, a method for preparing the suspension of porcine small intestinal mucosal brush border membrane will be described.

The preparation of a suspension of porcine small intestinal mucosal brush border membrane was performed in accordance with the method of Kessler et al. (Kessler M, Acuto O, Storelli C, Murer H, Muller M, Semenza G (1978) A modified procedure for the rapid preparation of efficiently transporting vesicles from small intestinal brush border membranes. Biochim Biophys Acta 506: 136-54).

For a porcine small intestine provided from Nagasaki Meat Inspection Center, mesenterial adipose tissue and the like adhered to the small intestine was gently cut off on an ice-cooled vat and about ½ of the proximal portion of the small intestine having a high disaccharidase activity was cut and divided in a length of 10 cm. Each of the divided pieces of small intestine was cut open in a longitudinal direction on an ice-cooled glass plate. After the lumen of the small intestine was washed with a physiological saline two or three times, water droplets were blotted using a paper towel. The pieces of small intestine were stacked on top of another in an opened state, and stored at −80° C. until the preparation of a suspension of porcine small intestinal mucosal brush border membrane.

The porcine small intestine (about 300 g) subjected to refrigerated storage was cut into small pieces in a frozen state using a kitchen knife. A 2 mM Tris-Cl buffer solution (pH 7.1) containing 50 mM mannitol was added in 19 times the amount of the porcine small intestine, and the mixture was homogenized using an ice-cooled Waring blender for about 90 seconds at an interval of 60 seconds.

Furthermore, the suspension was disintegrated using an ultrasonic device (US-4 manufactured by SND Co., Ltd.) for 20 minutes. Powdered calcium chloride was added to the suspension so that the final concentration was 10 mM, and the suspension was left to stand for 20 minutes in an iced state.

After that, the suspension was centrifuged at 3000×g at 4° C. for 15 minutes, and the resulting supernatant was further centrifuged at 27000×g at 4° C. for 30 minutes. To wash a small intestinal mucosal brush border membrane fraction of the precipitate, the precipitate was suspended with a 2 mM Tris-Cl buffer solution (pH 7.1) containing 50 mM mannitol, and the suspension was centrifuged at 27000×g at 4° C. for 30 minutes. After this process was repeated again, the resultant precipitate was suspended with a proper amount of 0.05 M phosphate buffer solution (pH 7.0), and the suspension was centrifuged at 27000×g at 4° C. for 30 minutes. Consequently, the 0.05 M phosphate buffer solution (pH 7.0) was substituted for tris(hydroxymethyl)aminomethane that has an inhibitory effect on a disaccharidase.

The resultant precipitate (purified brush border membrane vesicle) was suspended with a proper amount of 0.05 M phosphate buffer solution (pH 7.0). The suspension was dispensed into 10 mL plastic tubes and cryopreserved at −80° C. until the actual determination of a carbohydrate.

Hereinafter, a method for determining a carbohydrate according to Examples of the present invention will be described with reference to the drawings and the like, the method being conducted with the above-described the suspension of porcine small intestinal mucosal brush border membrane (animal-derived low-molecular-weight carbohydrate digestive enzyme).

Example 1

FIG. 1 shows a procedure of a method for determining a carbohydrate according to Example 1 of the present invention. More specifically, FIG. 1 shows a procedure for determining a carbohydrate by an enzymatic-HPLC method according to this Example.

In this Example, FOS (fructooligosaccharide) and IMO (isomaltooligosaccharide) were used as a nondigestible oligosaccharide (carbohydrate), and sucrose and lactose were used as a digestible saccharide (carbohydrate). That is, the method for determining a carbohydrate according to this Example which enables more accurate determination of a carbohydrate will be described using the nondigestible carbohydrates and digestible carbohydrates.

As shown in FIG. 1, in this Example, 1 g of nondigestible carbohydrate and 1 g of digestible carbohydrate were weighed, inserted into a tall-formed beaker (volume: 500 mL), and dissolved in 40 mL of 0.05 M MES/TRIS buffer solution (pH 6.3) (carbohydrate dissolution step).

After the dissolution, treatment with α-amylase was performed. Specifically, 200 μL of thermostable α-amylase (*Bacillus licheniformis*-derived), which is a digestive enzyme, was added thereto. The tall-formed beaker was covered with aluminum foil, and a reaction was caused under stirring with a DIGITAL HOT PLATE/STIRRER DP-1M (manufactured by AS ONE Corporation) for 30 minutes after the liquid temperature in the tall-formed beaker reached 95° C. (first reaction step).

After the first reaction step, 10 mL of 0.05 M MES/TRIS buffer solution (pH 6.3) was added to the tall-formed beaker. Cooling was performed to room temperature and then 200 µl, of protease (*Bacillus thermoproteolyticus*-derived) and 200 µl, of amyloglucosidase (*Aspergillus niger*-derived), which are digestive enzymes, were added thereto. The tall-formed beaker was covered with aluminum foil, and a reaction was caused under stirring for 30 minutes after the liquid temperature in the tall-formed beaker reached 60° C. (second reaction step).

After the second reaction step, treatment with a porcine small intestinal disaccharidase was performed. Specifically, to digest the oligosaccharide, an animal-derived low-molecular-weight carbohydrate digestive enzyme was added and a reaction was caused at 37° C. for 1 hour (third reaction step). Herein, an animal-derived small intestinal mucosal hydrolase was used as the "animal-derived low-molecular-weight carbohydrate digestive enzyme". More specifically, the suspension of porcine small intestinal mucosal brush border membrane (pH 7.0) prepared by ourselves as described above was used. Furthermore, before the third reaction step, protease was inactivated so that the animal-derived low-molecular-weight carbohydrate digestive enzyme was not decomposed by protease (inactivation step).

After the third reaction step, 95% ethanol heated to 60° C. in advance was added to the reaction solution in 4 times the amount of the reaction solution. The reaction solution was left to stand at room temperature accurately for 60 minutes to precipitate a polymer-like material (precipitation step).

After the precipitation step, the supernatant obtained through ethanol precipitation was separated into a residue and a supernatant by injecting the reaction solution into a glass filter having a filter layer formed of Celite in advance while aspiration was performed using ASPIRATOR A-3S (TOKYO RIKAKIKAI Co, Ltd.) (filtration step).

After the filtration step, residues left on the side wall of the tall-formed beaker and the glass filter were washed with 20 mL of 78% ethanol three times, 10 mL of 95% ethanol twice, and 10 mL of acetone twice, and the washings were collected in an Erlenmeyer flask (washing step).

Next, the alcohol of the collected supernatant (filtrate) was evaporated with a rotary evaporator (Rotavapor R-200 manufactured by SIBATA SCIENTIFIC TECHNOLOGY LTD.) (evaporation step).

Then, the solution subjected to the evaporation was dissolved in a small amount of water and desalted with an amphoteric ion-exchange resin (Amberlite MB-3 manufactured by ORGANO Corporation) (desalting step).

Subsequently, the collected solution was measured using a graduated cylinder so as to have a volume of 50 mL, and then impurities such as proteins were filtered with a membrane filter (Millex-GV Non-Sterile 0.22 µm×13 mm, Millipore Co., USA) to obtain a test sample for HPLC.

An analysis performed to determine each carbohydrate using HPLC was as follows.

Measuring instrument: LC-20AD (manufactured by SHIMADZU Corporation)
Column: Shodex SUGAR KS-802 (8.0ϕ×300 mm, manufactured by Showa Denko K.K.)
Column temperature: 70° C.
Mobile phase: $H_2O$
Flow rate: 0.5 mL/min
Amount of sample injected: 10 µL
Detector: Refractive Index Detection RID-10A (manufactured by SHIMADZU Corporation)

An nondigestible carbohydrate and a digestible carbohydrate that were not decomposed by a series of treatments with enzymes in the method for determining a carbohydrate (a refined method of an enzymatic-HPLC method) according to this Example were analyzed using a Shodex SUGAR KS-802 column at a column temperature of 70° C. A solution prepared by dissolving an nondigestible carbohydrate in distilled water and a solution prepared by dissolving a digestible carbohydrate in distilled water (5.0 mg/mL each) were used as a standard solution.

Figure 2:
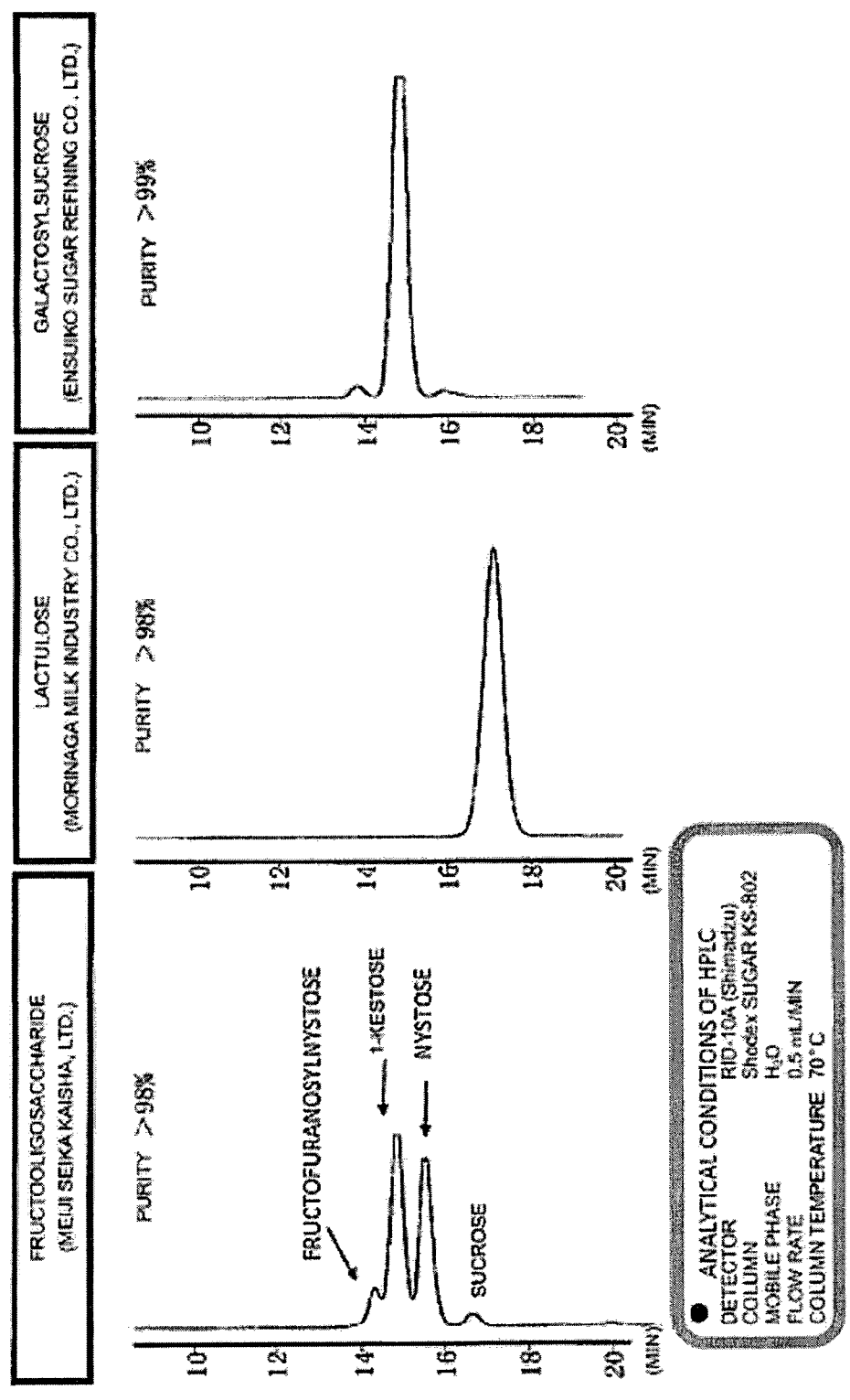
FIG. 2 shows chromatographs of fructooligosaccharide, lactulose, and galactosylsucrose used as standard substances.
Figure 3:
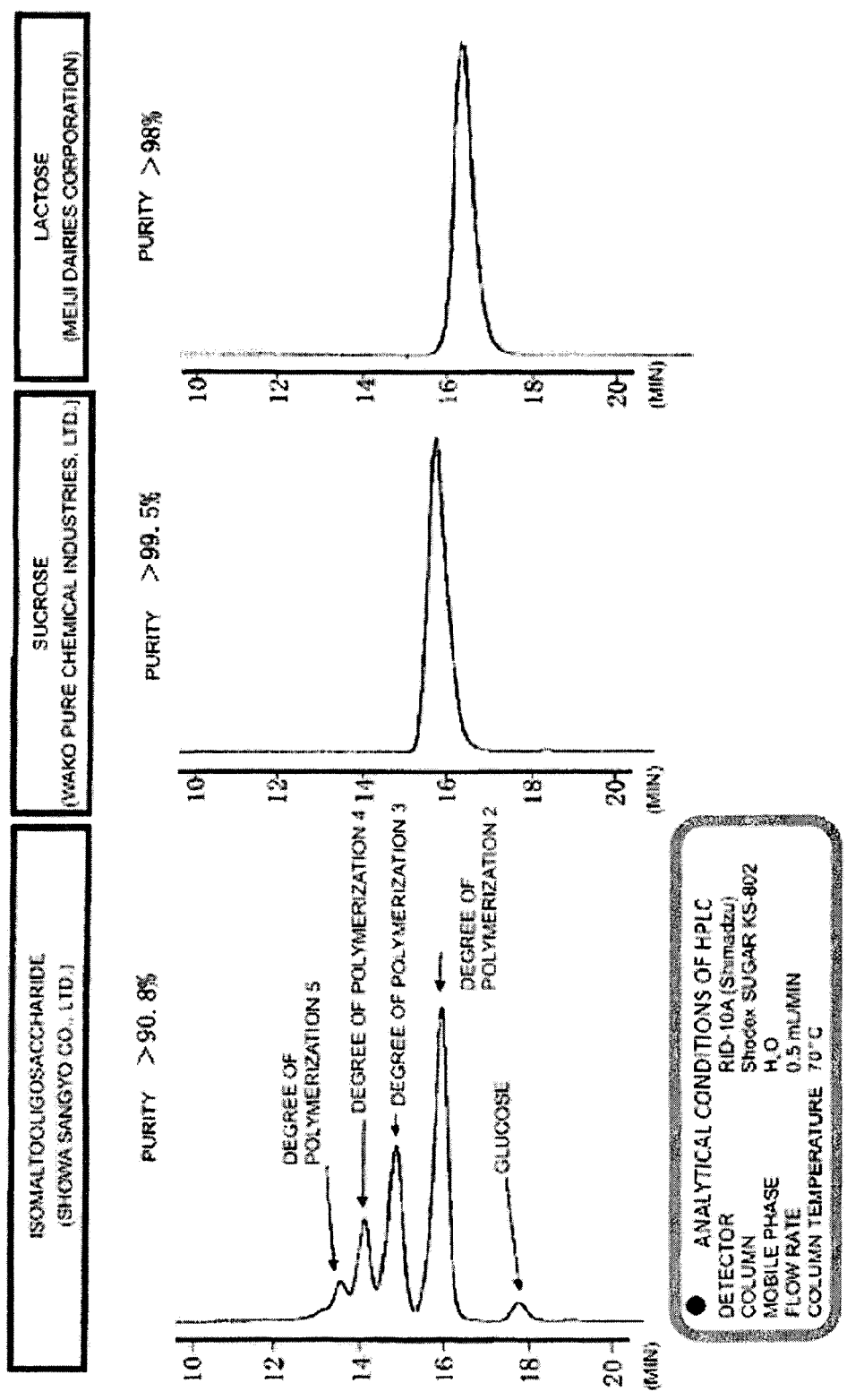
FIG. 3 shows chromatographs of isomaltooligosaccharide, sucrose, and lactose used as standard substances.

Herein, FIGS. 2 and 3 show elution profiles of standard substance solutions used to determine a nondigestible carbohydrate and a digestible carbohydrate by HPLC.

The recovery percentage of undigested carbohydrates after the treatments with enzymes was calculated from the formula below.

Recovery percentage of undigested carbohydrate (%)= $(((A/B)\times\text{dilution ratio})/\text{sample weight }(g))\times100$ A: a peak area of the carbohydrate after the treatments with enzymes
B: a peak area of the standard substance solution The method for determining a carbohydrate according to this Example has the above-described configuration, whereby the following results can be obtained.

Figure 4:
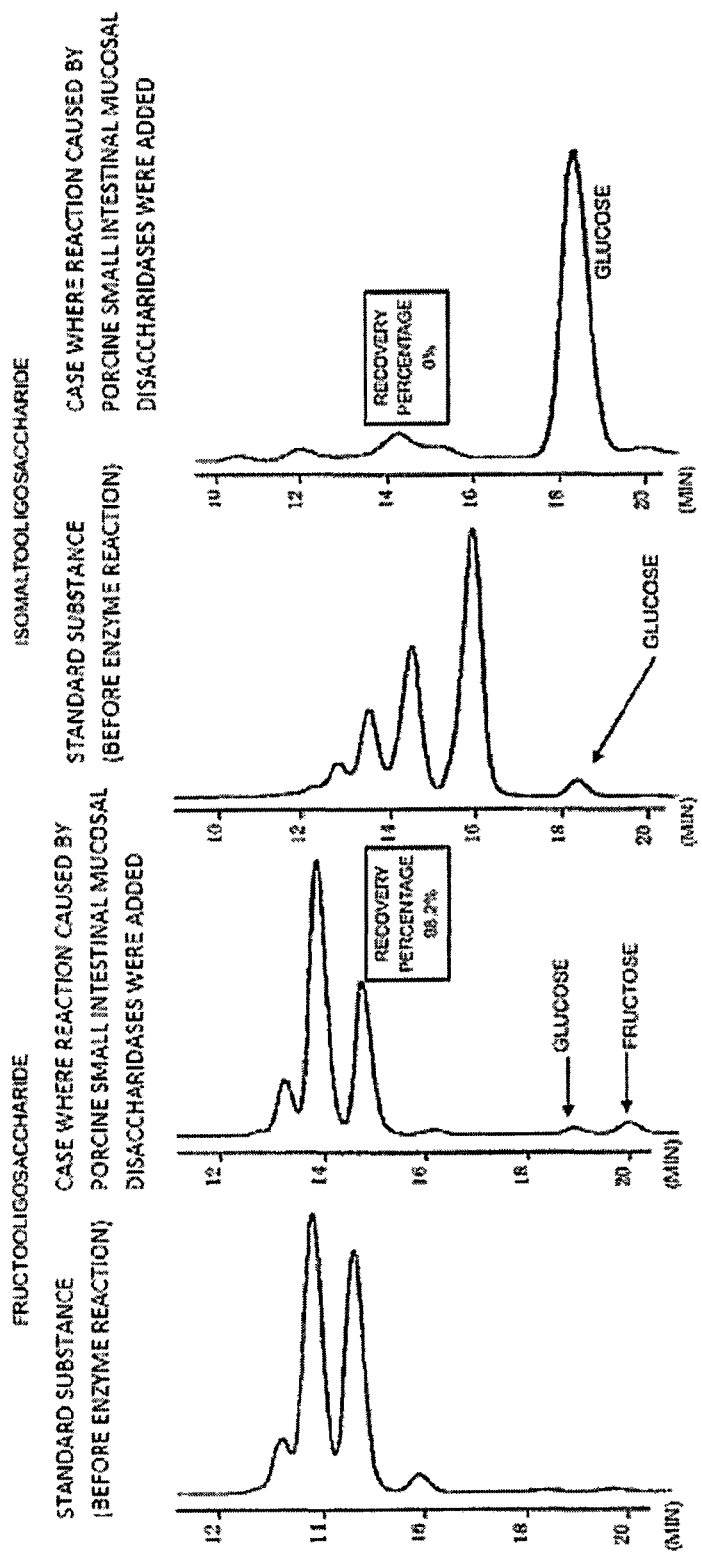
FIG. 4 is a chromatograph showing the determination results of nondigestible carbohydrate fractions regarding fructooligosaccharide (FOS) and isomaltooligosaccharide (IMO) in the case where the method for determining a carbohydrate according to Example 1 of the present invention is used. This Figure shows determination of nondigestible carbohydrate fractions of fructooligosaccharide and isomaltooligosaccharide when employing the enzymatic-HPLC method according to Example 1, to which porcine small intestinal mucosal disaccharidase reaction was added. Recovery percentage is a percentage of nondigestible carbohydrate fraction determined after the enzyme reaction when nondigestible carbohydrate fraction of the standard substance is assumed to be 100%. Nearly 100% of fructooligosaccharide was determined as a nondigestible carbohydrate fraction, and isomaltooligosaccharide was not determined as a nondigestible carbohydrate fraction because it was completely digested by porcine small intestinal disaccharidases.
Figure 5:
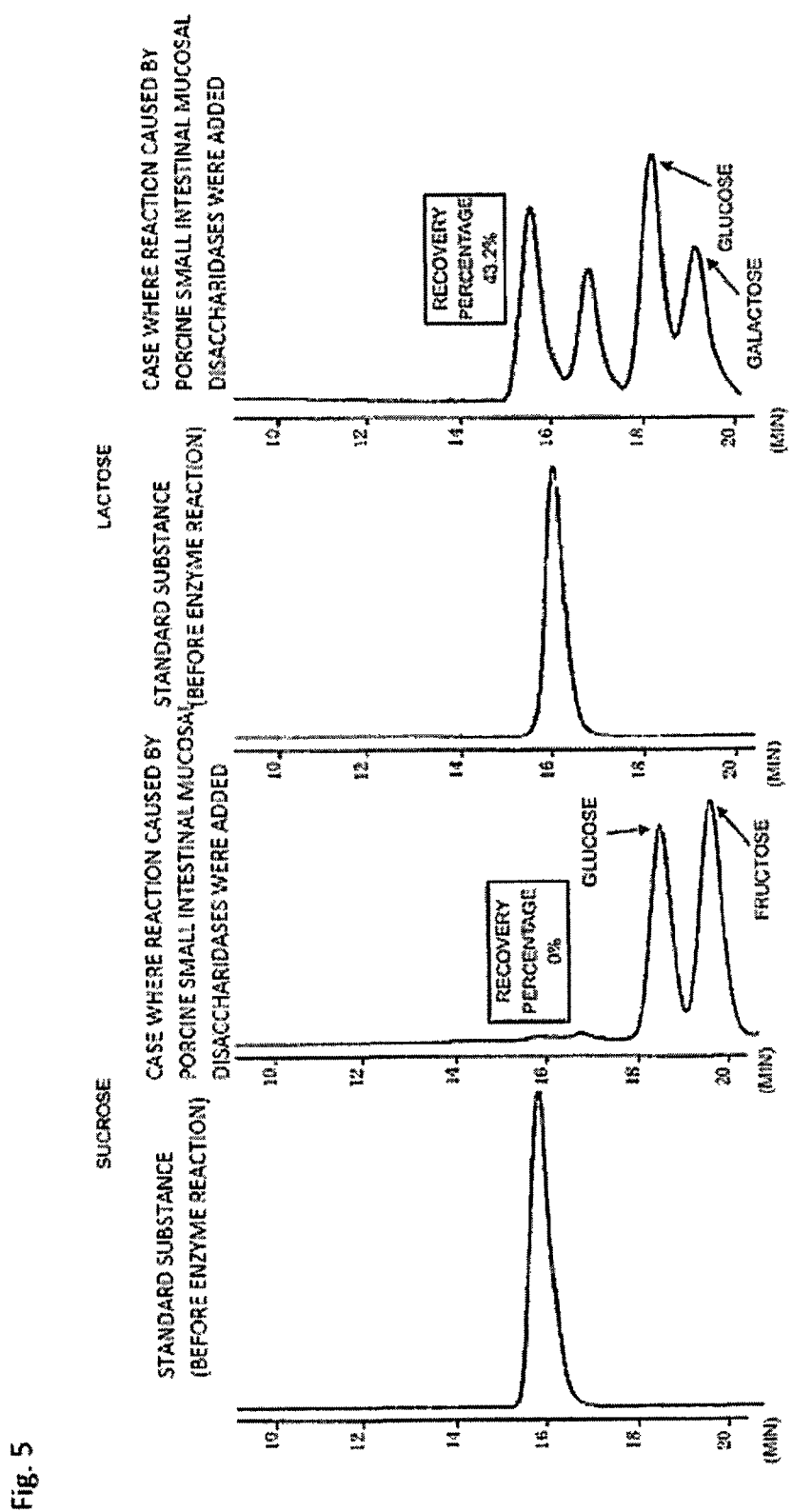
FIG. 5 is a chromatograph showing the determination results of nondigestible carbohydrate fractions regarding sucrose and lactose in the case where the method for determining a carbohydrate according to Example 1 of the present invention is used. This Figure shows determination of nondigestible carbohydrate fractions of sucrose and lactose when employing the enzymatic-HPLC method according to Example 1, to which porcine small intestinal mucosal disaccharidase reaction was added. Recovery percentage is a percentage of nondigestible carbohydrate fraction determined after the enzyme reaction when nondigestible carbohydrate fraction of the standard substance is assumed to be 100%. Sucrose was not determined as nondigestible carbohydrate fraction because it was completely digested by porcine small intestinal mucosal disaccharidases. Lactose was digested about 50%.
Figure 6:
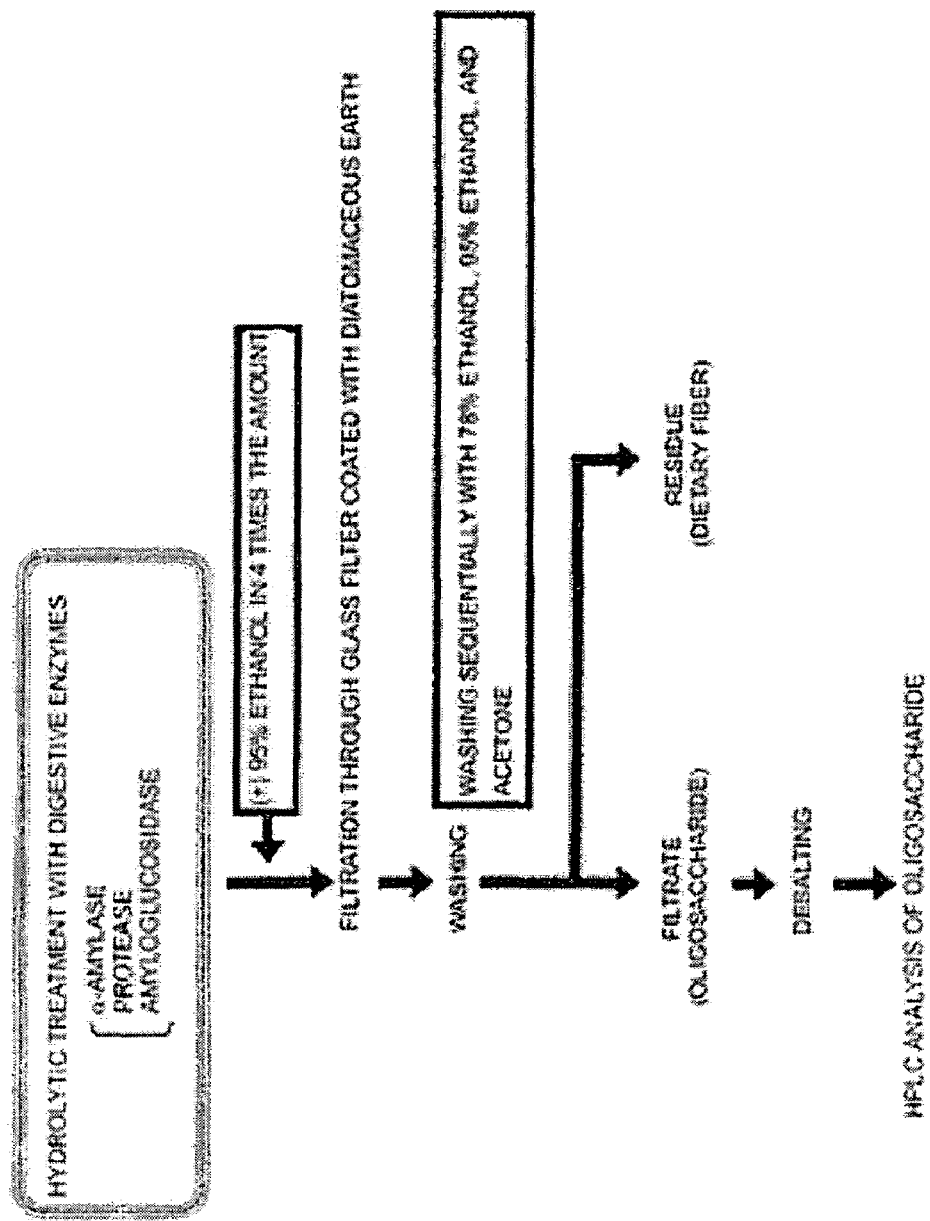
FIG. 6 shows a procedure of an enzymatic-HPLC method according to the related art achieved by partly changing a dietary fiber determination method that uses an enzyme-gravimetric method of Prosky. This is a dietary fiber determination method. In other words, this Figure shows an oligosaccharide determination method achieved by partly changing the enzyme-gravimetric method of Prosky. This shows a procedure of oligosaccharide determination method performed by enzymatic-HPLC method achieved by partly refining the enzyme-gravimetric method of Prosky which is a dietary fiber determination method.

FIGS. 4 and 5 show the results of the method for determining a carbohydrate according to this Example. Herein, FIG. 4 is a graph showing the determination results of nondigestible carbohydrate fractions regarding fructooligosaccharide (FOS) and isomaltooligosaccharide (IMO) in the case where the method for determining a carbohydrate according to this Example was used. FIG. 5 is a graph showing the determination results of nondigestible carbohydrate fractions regarding sucrose and lactose in the case where the method for determining a carbohydrate according to this Example was used.

As is clear from these drawings, FOS was hardly digested even if the porcine small intestine-derived disaccharidase was added to the enzyme reaction system, and the recovery percentage of undigested matter was as extremely high as 98.2% (refer to FIG. 4).

On the other hand, IMO, which is a nondigestible carbohydrate, was almost completely digested by adding the porcine small intestine-derived disaccharidase to the enzyme reaction system, and only glucose, which is a minimum constitutional unit of IMO, was detected (refer to FIG. 4).

As in the case of IMO, sucrose, which is digested by sucrase, was also almost completely digested by adding the porcine small intestine-derived disaccharidase to the enzyme reaction system (refer to FIG. 5).

However, lactose, which is digested by lactase, was digested only 56.8% because the lactase activity of the suspension of porcine small intestinal mucosal brush border membrane was low. Furthermore, it was confirmed that, by causing lactose to react with the suspension of porcine small intestinal mucosal brush border membrane, a disaccharide other than lactose was newly produced (refer to FIG. 5).

As described above, it is believed that a carbohydrate digestive enzyme used in an enzymatic-HPLC method according to the related art can digest high-molecular-weight polysaccharides but cannot easily digest low-molecular-weight oligosaccharides due to the nature thereof. Therefore, despite the fact that IMO is easily digested by a small intestinal mucosal enzyme of humans and rats, only a small amount of IMO is hydrolyzed by a hydrolase used to determine dietary fiber according to the related art. This shows that, in the enzymatic-HPLC method that is an AOAC official method, there is a problem in that both of the digestible and nondigestible oligosaccharides are determined as nondigestible oligosaccharides.

In contrast, according to this Example, a method for determining a carbohydrate that solves the above-described problem of the related art and that enables more accurate determination of a carbohydrate can be achieved. In other words, since a carbohydrate digestive enzyme currently used in the enzymatic-HPLC method lacks α-glucosidase and β-galactosidase that digest low-molecular-weight carbohydrates, by adding both of them to the reaction system, a carbohydrate (oligosaccharide) can be determined more accurately. In this Example, therefore, a suspension of porcine small intestinal mucosal brush border membrane (porcine small intestinal mucosal digestive enzyme) is used.

More specifically, this Example provides a method for determining a carbohydrate using a digestive enzyme, characterized in that the digestive enzyme is an animal-derived low-molecular-weight carbohydrate digestive enzyme. This Example also provides a method for determining a carbohydrate using a digestive enzyme, characterized by including a first reaction step using thermostable α-amylase, a second reaction step using protease and amyloglucosidase, and a third reaction step using an animal-derived low-molecular-weight carbohydrate digestive enzyme. Furthermore, in this Example, an animal-derived small intestinal mucosal hydrolase is used as the low-molecular-weight carbohydrate digestive enzyme.

Based on such a configuration, according to this Example, a nondigestible carbohydrate and a digestible carbohydrate can be separately determined, and thus a nondigestible oligosaccharide can be determined accurately.

The feature of this Example is to add an animal-derived low-molecular-weight carbohydrate digestive enzyme to a hydrolytic reaction system. Therefore, any kit (any kit for determining a carbohydrate) belongs to the technical scope of the present invention as long as the feature is satisfied.

Specifically, the present invention provides a kit for determining a carbohydrate including a digestive enzyme, characterized in that an animal-derived low-molecular-weight carbohydrate digestive enzyme is included as the digestive enzyme. The kit for determining a carbohydrate according to the present invention is characterized by including thermostable α-amylase, protease, amyloglucosidase, and an animal-derived small intestinal mucosal hydrolase as the digestive enzyme. Furthermore, in the kit for determining a carbohydrate according to the present invention, an animal-derived small intestinal mucosal hydrolase is preferably included as the digestive enzyme.

Other Examples

The present invention is not limited to the above-described embodiments and Examples (hereinafter referred to as "embodiments or the like"). Various modifications can be made according to need, and they are all included in the technical scope of the present invention.

For example, in the embodiments or the like, the case where "a porcine low-molecular-weight carbohydrate digestive enzyme (suspension of porcine small intestinal mucosal brush border membrane)" is used as "an animal-derived low-molecular-weight carbohydrate digestive enzyme" has been described, but the present invention is not limited to the configuration. If the activity is similar to that of humans, low-molecular-weight carbohydrate digestive enzymes derived from "other animals" can also be used. Thus, small intestinal mucosal hydrolase of other animals such as a rat and a cow may be used.

Industrial Applicability

It has become obvious that dietary fiber and nondigestible oligosaccharides/sugar alcohols have a specific physiological effect on health that is different from conventional carbohydrates and are significantly related to the prevention of a lifestyle-related illness and the like. In addition, there has been a growing interest in being health conscious because of a change in a sense of values of people. Thus, food manufacturers and pharmaceutical manufacturers have been actively developing functional foods such as foods for specified health uses that emphasize various physiological functions.

Under these circumstances, many foods for specified health uses to which dietary fiber and nondigestible oligosaccharides/sugar alcohols are added are approved. For processed foods such as foods for specified health uses, the nutritive ingredients have to be indicated in accordance with the nutrition labeling standards provided in the Health Promotion Law. Since the development of functionality of components added to processed foods depends on the contents of the components added thereto, the determination is important.

However, it is believed that an overestimation is made in a dietary fiber determination method and a nondigestible oligosaccharide determination method, which are current official methods (according to the related art). This may lead to false labeling. Consumers have a right to know correct information based on scientific grounds.

Accordingly, by using the above-described method for determining a carbohydrate and kit for determining a carbohydrate according to the present invention, a nondigestible carbohydrate and a digestible carbohydrate can be separately determined accurately, which can provide correct information to consumers.

The invention claimed is:

1. A method for determining whether a carbohydrate is a non-digestible oligosaccharide, comprising:
   (a) reacting the carbohydrate with thermostable α-amylase; then
   (b) reacting the reaction product of step (a) with protease and amyloglucosidase; then
   (c) reacting the reaction product of step (b) with a suspension of an animal-derived low-molecular-weight carbohydrate digestive enzyme, said suspension having been prepared by surgical removal of a portion of the intestine of an animal, followed by homogenization, ultrasonic disintegration and centrifugation thereof, and then
   (d) determining whether the carbohydrate is a non-digestible oligosaccharide by comparing high-performance liquid chromatography of the carbohydrate prior to step (a) with high-performance liquid chromatography of the reaction product of step (c).

2. The method for determining a carbohydrate according to claim 1, wherein the low-molecular-weight carbohydrate digestive enzyme is an animal-derived small intestinal mucosal hydrolase.

3. A kit for determining a carbohydrate including a digestive enzyme, comprising:
   thermostable α-amylase;
   protease;
   amyloglucosidase; and
   a suspension of an animal-derived low molecular-weight carbohydrate digestive enzyme, said suspension having been prepared by surgical removal of a portion of the intestine of an animal, followed by homogenization, ultrasonic disintegration and centrifugation thereof.

4. The kit for determining a carbohydrate according to claim 3, wherein the animal-derived low-molecular weight carbohydrate digestive enzyme is an animal-derived small intestinal mucosal hydrolase.

5. The method for determining a carbohydrate according to claim 2, wherein the portion of the intestine of the animal is the proximal portion of the small intestine of an animal.

6. The kit for determining a carbohydrate according to claim 4, wherein the portion of the intestine of the animal is the proximal portion of the small intestine of an animal.

* * * * *